United States Patent [19]
Lee et al.

[11] Patent Number: 5,696,312
[45] Date of Patent: Dec. 9, 1997

[54] ACCELERATED IMPACT TESTING APPARATUS

[75] Inventors: Nathan J. Lee, Escondido, Calif.; William G. Pitt, Orem, Utah

[73] Assignee: Brigham Young University, Provo, Utah

[21] Appl. No.: 556,584

[22] Filed: Nov. 13, 1995

[51] Int. Cl.$^6$ ..................................................... G01N 3/00
[52] U.S. Cl. ........................................ 73/12.13; 73/12.02
[58] Field of Search ............................. 73/12.01, 12.02, 73/12.04, 12.06, 12.09, 12.13; 473/316

[56] References Cited

U.S. PATENT DOCUMENTS

| | | | |
|---|---|---|---|
| 1,703,507 | 2/1929 | Barnhart | 73/12.04 X |
| 1,753,532 | 4/1930 | Reid et al. | 73/12.06 |
| 2,610,504 | 9/1952 | Nigh . | |
| 2,660,880 | 12/1953 | Vivian . | |
| 2,755,658 | 7/1956 | Brown . | |
| 3,226,974 | 1/1966 | Bresk et al. | 73/12.06 |
| 3,444,729 | 5/1969 | Shobert | 73/12.04 X |
| 3,566,668 | 3/1971 | Browning et al. . | |
| 3,855,842 | 12/1974 | Imabori et al. | 73/12.02 X |
| 4,062,222 | 12/1977 | Solheim | 73/12.02 |
| 4,261,566 | 4/1981 | MacDougall | 273/77 A |
| 4,523,759 | 6/1985 | Igarashi | 273/169 |
| 4,640,120 | 2/1987 | Garritano et al. . | |
| 4,711,754 | 12/1987 | Bednar . | |
| 4,996,867 | 3/1991 | Miyamae | 73/12.02 X |
| 5,247,835 | 9/1993 | Howell . | |

*Primary Examiner*—Elizabeth L. Dougherty
*Attorney, Agent, or Firm*—William W. Haefliger

[57] ABSTRACT

Accelerated impact testing apparatus which simulates the dynamic strain in golf clubs, shafts and other specimens by rapidly transferring kinetic energy to the specimen from an instrumented tup that is free to rebound. The specimen is held in place by two holding fixtures uniquely designed to provide the appropriate boundary and support conditions for the transient strain to propagate in a manner similar to that of the actual application e.g. a golf club striking a ball. Force applied to the tup is generated by compressing a spring to a predetermined length and releasing its energy through a rapidly actuated latch. Actual force applied as a function of time is measured by a load cell located in the tup and the tup velocity just prior to impact is computed from a velocity sensor signal. Acceleration of the impact event is also recorded as well as strain levels in the shaft.

14 Claims, 9 Drawing Sheets

ACCELERATED IMPACT TESTING APPARATUS

BACKGROUND OF THE INVENTION

This invention relates to materials testing and pertains, more specifically, to dynamic testing at various strain rates and loading conditions and the controlling of velocity of an impactor and the maximum deflection of the specimen under test.

The increased demand for varied materials and manufacturing processes has required that apparati be developed to meet the need for testing devices which realistically simulate the dynamic strain environment generated in various applications e.g. a golf shaft when striking a ball, yet, are capable of evaluating a wide range of materials, and are economical and characterized by ease of use in the workplace.

The dynamic testing of materials has been carried out in the past by various impact apparati, however, to applicant's knowledge none employ an improved cantilever type simple support configuration for the specimen, and mode of operation as embodied in the present apparatus. There is need for such an improved support configuration which in use more closely simulates actual strain and strain rates applied to materials during use in high strain and high strain rate applications. Furthermore, there is need for impact test apparatus and methods useful for the bending of tubular specimens. Strain and strain rates produced in tubular specimens tested by apparati using long cantilevered and rigidly fixed test specimens do not duplicate with sufficient validity the dynamic strain environment generated in the actual applications.

SUMMARY OF THE INVENTION

It is a major object of the invention to provide accelerated impact testing apparatus and method meeting the above need. Such apparatus is typically usable with respect to impact testing of a golf shaft having first and second ends, and includes:

a) primary means to support the shaft intermediate the first and second ends, b) secondary means to support the shaft near it second end and defining a downwardly curved support channel into which the second end of the shaft is downwardly displaceable in response to impact loading, and c) a hammer located to be driven toward the shaft near its second end to deliver impact loading to the shaft.

Another object is to provide an anvil on the second end of the shaft to be struck by the hammer (i.e. tup).

Yet another object is to provide a spring located to be compressed and to suddenly expand toward the hammer, and a latch to retain the hammer until expanding spring force is delivered to the hammer, and to release the hammer in response to such delivery.

An additional object includes provision of sensor means to sense the velocity of hammer travel as it delivers such impact loading, and also to provide circuitry responsive to such velocity sensing to compute for example the kinetic energy of the hammer at impact, or for velocity recording.

Further objects include provision of apparatus that improves upon drop-tower type, as well as hydraulically and pneumatically associated type testers; apparatus for impact testing of specimens having a wide variety of configurations and over a large range of speeds, and to enable realistic and accurate data to be collected; provision of apparatus for testing golf shaft durability without having to attach a head to the shaft; provision of means to allow higher rates of testing of golf shafts, using a relatively small machine; provision of means to allow for realistic stress and stress rates to be applied to golf shaft, or other tubular specimens under test; provision of a support system which allows stresses to be distributed in a specimen golf club shaft and in a realistic way so as to simulate a golf club striking a ball; and provision of means whereby the maximum strain applied to the specimen is limited by adjustable bumper stops.

The invention will be understood more fully in the following detailed description of a preferred embodiment illustrated in the accompanying drawings, in which:

GENERAL ORGANIZATION

Referring first to FIGS. 1, 2, 8, and 10, the illustrated apparatus 100 is usable to enable impact testing of a golf club shaft, seen at 101. The shaft has a first end 101a to support a hand grip (not shown) and a second end 101b to which a golf club head (not shown) is to be assembled. Typically, shaft end 101b, is assembled into a supporting tubular hosel of a golf club head (see U.S. Pat. No. 5,163, 682 incorporated herein by reference), and the hosel may be located within the head, or externally thereof. The shaft end portion 101c adjacent portion 101b is typically located immediately above the hosel, and is not directly supported by the hosel in use, whereby it is subjected to a high degree of shock stress, i.e. bending stress, in response to high speed impact of the golf club head with a golf ball. Also, shaft lower end portion 101b is typically tubular, and has reduced diameter as compared with the larger diameter of the first end 101a. It is therefor desirable to impact test such a shaft, as by side impacting second end portion or portions 101b and/or 101c, and as under shaft production conditions, to determine that a selected shaft is sufficiently durable to withstand repeated use under ball striking conditions, i.e. during play. The shaft may consist of graphite or composite material, as is known.

Figure 10:
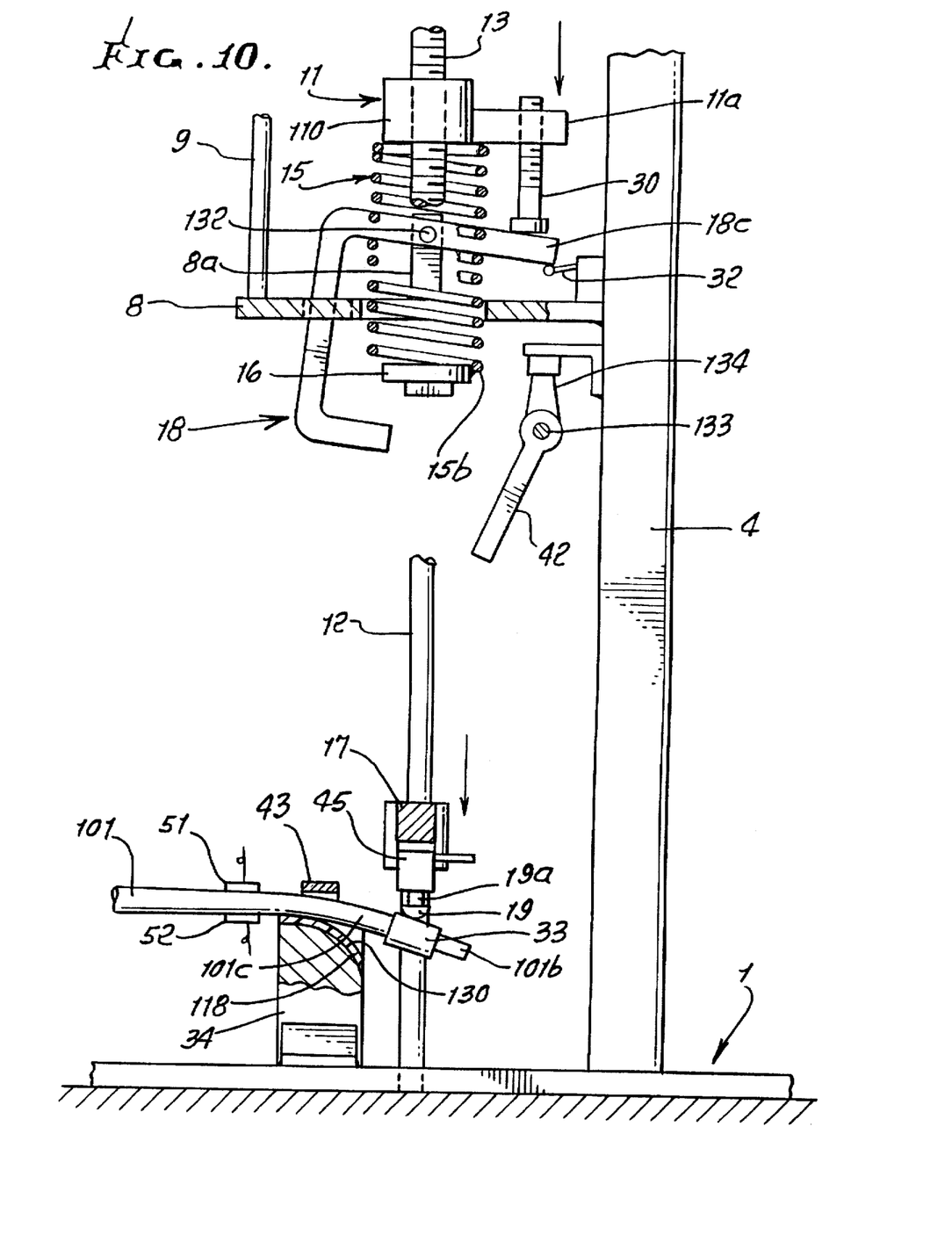
FIG. 10 is an enlarged fragmentary side view of the apparatus, similar to FIG. 2, but with the components in another i.e. released operating position.

Basically, the apparatus shown comprises:

a) primary means to support the shaft 101 intermediate its first and second opposite ends (see for example clamp support at 44 on fixture 35), b) secondary means to support the shaft 101 near its second end and defining a downwardly curved support channel into which the second end of the shaft is downwardly displaceable in response to impact loading (see for example holding bracket 43 on holding fixture 34; and U-shaped cross-section channel 130 curved downwardly in FIG. 10 to receive the sidewardly downwardly deflected shaft end portion 101c), c) and a hammer or tup located to be driven downwardly toward the shaft near its second end to deliver shaft bending impact loading to the shaft. (See for example tup 19 carried as by cross-head 17 in FIG. 10).

Accordingly, if the end portion of the sample shaft that is deflected into and along the U-shaped channel 130 does not fracture, it is determined that such sample shaft is acceptable, and that other production shafts, on a production line from which the sample was selected, are also acceptable. Downwardly curved channel 130 simulates the curvature of shaft bending above the hosel when golf club head strikes a golf ball at high speed.

Note also, the provision of an anvil sleeve 33 fitted on the end portion of the shaft 101 to receive tup impact loading; the spring 15 to be compressed and to suddenly expand toward the hammer or tup to drive the latter downwardly, and latch 18 that suddenly releases the spring and crosshead 17.

DETAILED DESCRIPTION

Referring now to FIGS. 1, 2, 8 and 10, a frame plate indicated at 1 is carried by and secured to two base members 1a which in turn incorporate leveling feet 3, at opposite ends of base member 2. Vertical member 4 of the apparatus is attached to frame 1 and provides an attaching surface 4a for a top horizontal frame plate 6 and horizontal frame mid plate 8. Mid plate 8 and top plate 6 are attached together at their outermost ends as by support rods 9.

A motor 5 is carried at the topmost surface of drive assembly 22 which has secure attachment to top plate 6. Torque from motor 5 is transmitted through a flexible coupling 14 to vertical ball screw 13. The vertical alignment of ball screw 13 is maintained by two pillow block bearings 23 that are contained in pillow block bearing housing 24. Bearings 23 are attached to the rear surface of drive assembly 22.

Figure 1:
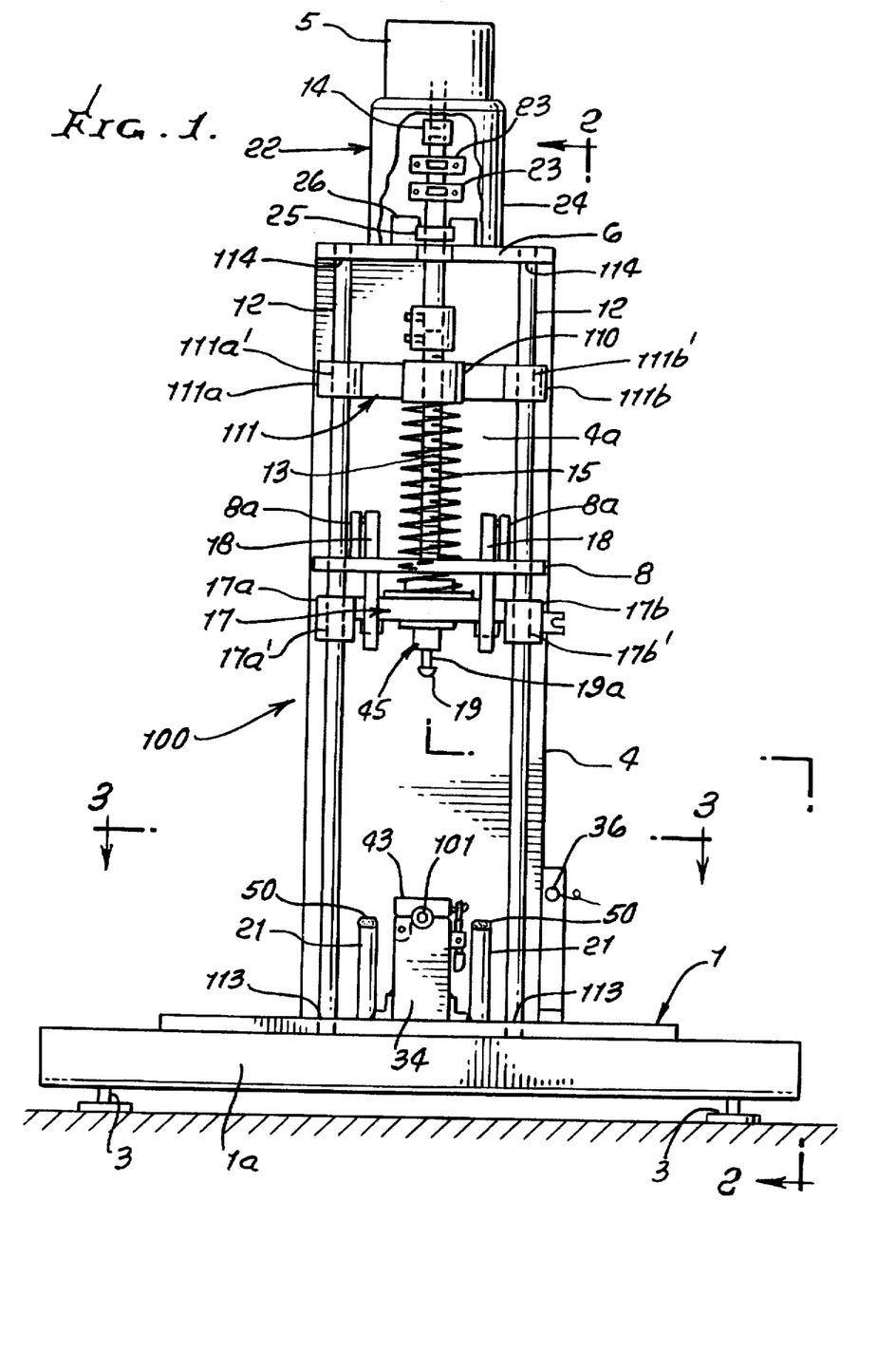
FIG. 1 is a front elevational view of accelerated impact testing apparatus embodying the invention.
Figure 2:
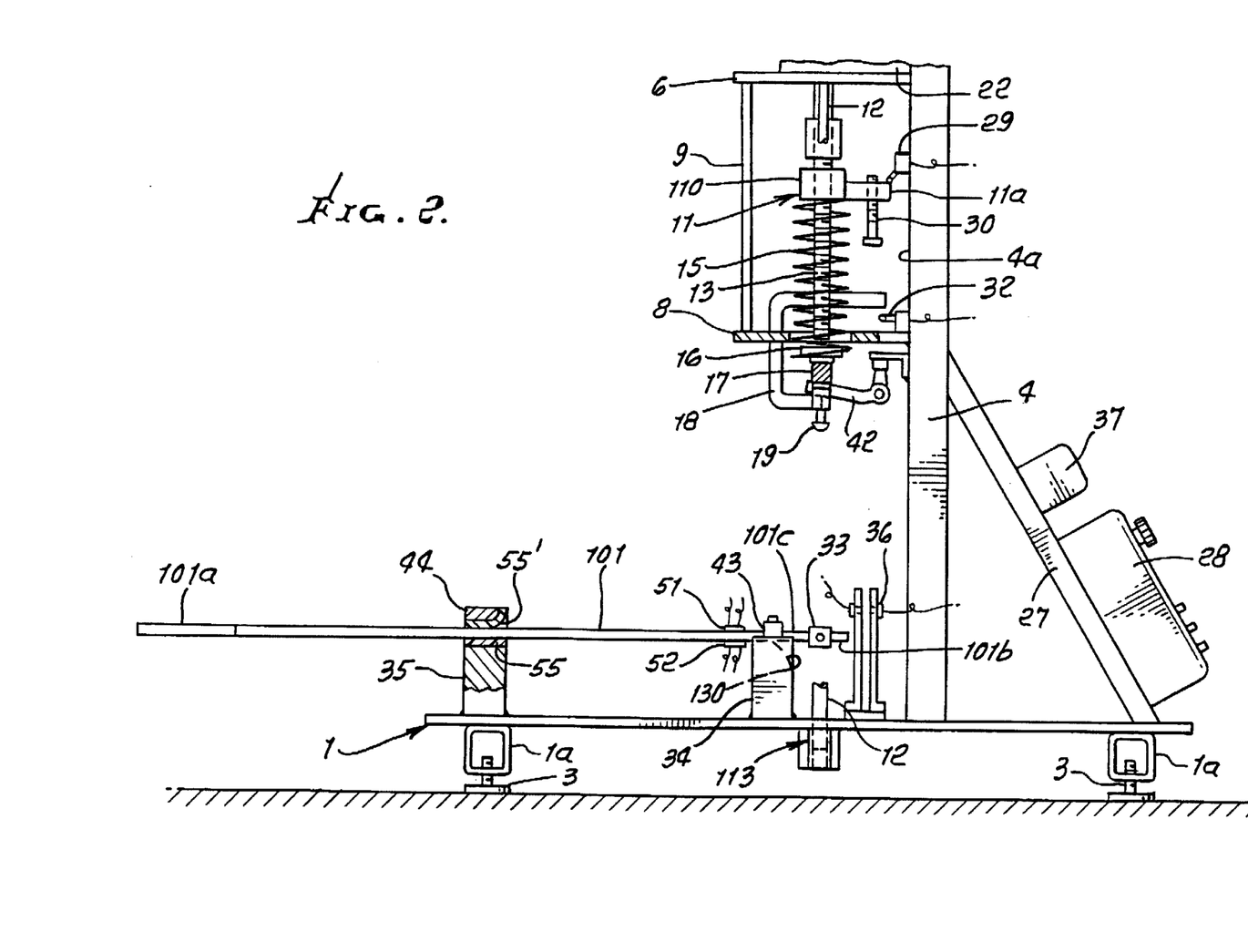
FIG. 2 is a side elevational view, partially sectioned, of the accelerated impact testing apparatus, taken on lines 2—2 of FIG. 1.

As shown in FIGS. 1 and 2, a nut 110 passes the screw, and is threadably engaged therewith. The nut is carried by a horizontal crosshead 111. Opposite end portions 111a and 111b of the crosshead define vertical bores at 111a' and 111b' that slidably receive the vertical guide rails or rods 12. The latter have opposite ends attached to the frame at 113 and to the plate 6 at 114.

Figure 11:
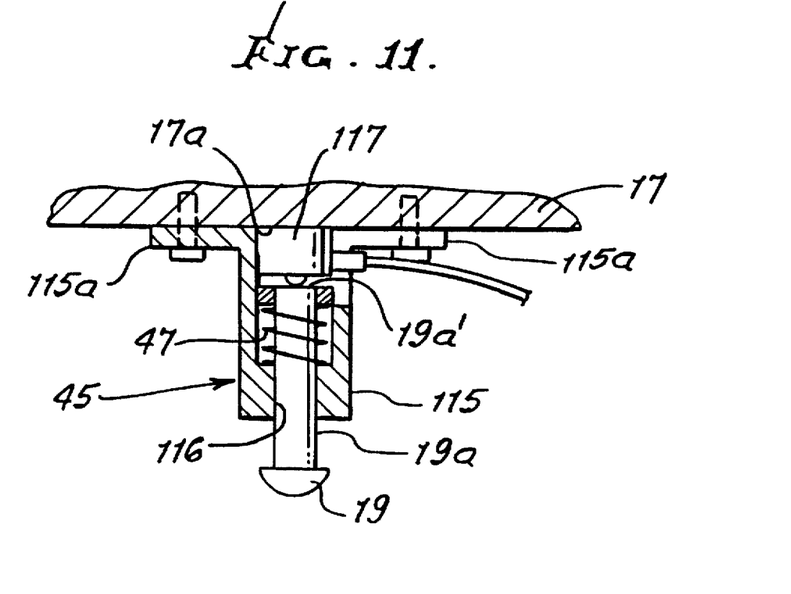
FIG. 11 is an enlarged elevational cross-sectional view of the tup assembly.

Compression spring 15 extending about the screw has its upper end 15a bearing against the lower end of the nut 110, and its lower end 15b engages a pressure plate 16, as seen in FIG. 1. That plate is carried by a crosshead 17 having opposite end portions 17a and 17b that define bores 17a' and 17b' receiving and guiding along the guide rails 12. Linear bearings may be provided at 17a' and 17b'. Connected to the underside of the crosshead 17 is a tup assembly 45 (see FIG. 11) that includes downwardly convex tup 19, tup rod 19a, a housing 115 defining a bore 116 passing rod 19a, a spring 47 in the housing 115, and a load cell 117 in the housing between the upper rod 19a' of the rod 19a and the lower side 17a of the crosshead 17. The housing has flanges 115a attached to the crosshead, as shown. Accordingly, as tup 19 impacts anvil sleeve 33 on the shaft 101 (see FIG. 10), reaction force is transmitted to the load cell, to produce impact force measurement. Note the end portion 101b of shaft 101 being bent downwardly in FIG. 10, along U-cross section channel defined by synthetic resinous (for example DELRIN) channel lining 118. The downwardly convex surface of the tup accommodates to the sleeve 33 as the latter is deflected downwardly.

Upward force resulting from spring 15 compression is taken by thrust bearing 25 contained in thrust bearing housing 26 attached to top plate 6. Top plate 6 provides support to the upper ends of guide rails 12 which pass through mid plate 8. The bottom ends of guide rails 12 are attached to frame 1, as referred to above.

Turning now to FIG. 2, angled support bars 27 are provided and are secured to frame 1 and vertical member 4 to support vertical member 4 and to provide a mounting surface for motor controller 28 and amplifier 37. When spring compression assembly 11 is in its uppermost position as seen in FIG. 2, it activates upper limit switch 29 which in turn provides a signal to disconnect electrical power transmission to motor 5. Note flange 11a projecting sidewardly from nut 110, toward the limit switch.

Figure 3:
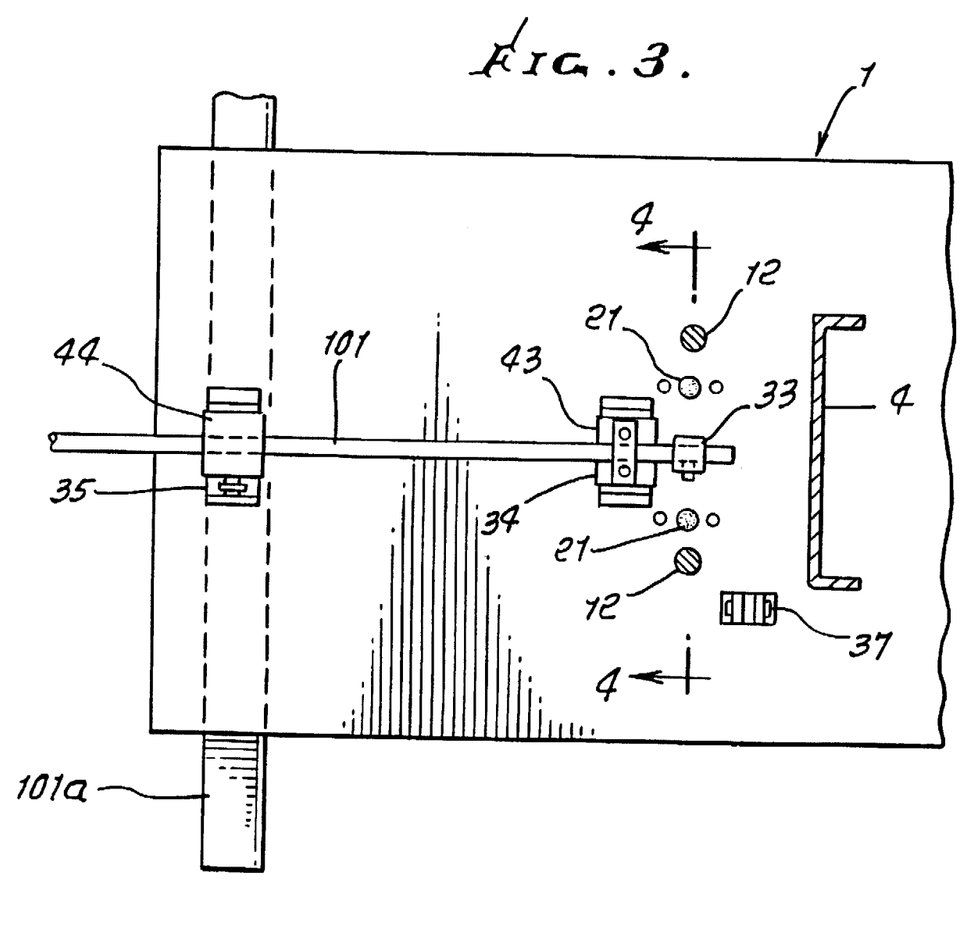
FIG. 3 is a partial top plan view of the accelerated impact testing apparatus, taken on lines 3—3 of FIG. 1.

Test specimen shaft 101 is held in place by front holding fixture 34 and rear holding fixture 35 (see FIGS. 2 and 3). The test specimen is held from moving during and after impact force is applied by restraining bracket 43 and restraining clamp 44. Smooth, downward groove such as channel at 130 is contoured onto front holding fixture 34 to establish the boundary conditions for the test, including preventing the test specimen end portions 101c and 101b from bending sideways, but allowing them to bend downward. The channel also prevents sharp local bending. The groove of front holding fixture 34 and the bottom of restraining bracket 43 are lined with durable synthetic resinous material such as DELRIN to ensure that no failures originate in the test specimen, due to sharp edges. Rear holding fixture 35 is spaced approximately eighteen (18) inches from the tup 19 strike point (as when a golf club shaft is under test) to assure that no strain wave reflected from rear holding fixture 35 arrives back at the strike point, during the impact event including bending of the shaft. Restraining clamp 44 may contain elastomer cushion 55 to further insure no localized damage is caused during the test. Note upward curvature at 55' to allow local upward bending or bowing of the shaft, between 43 and 44.

Figure 8:
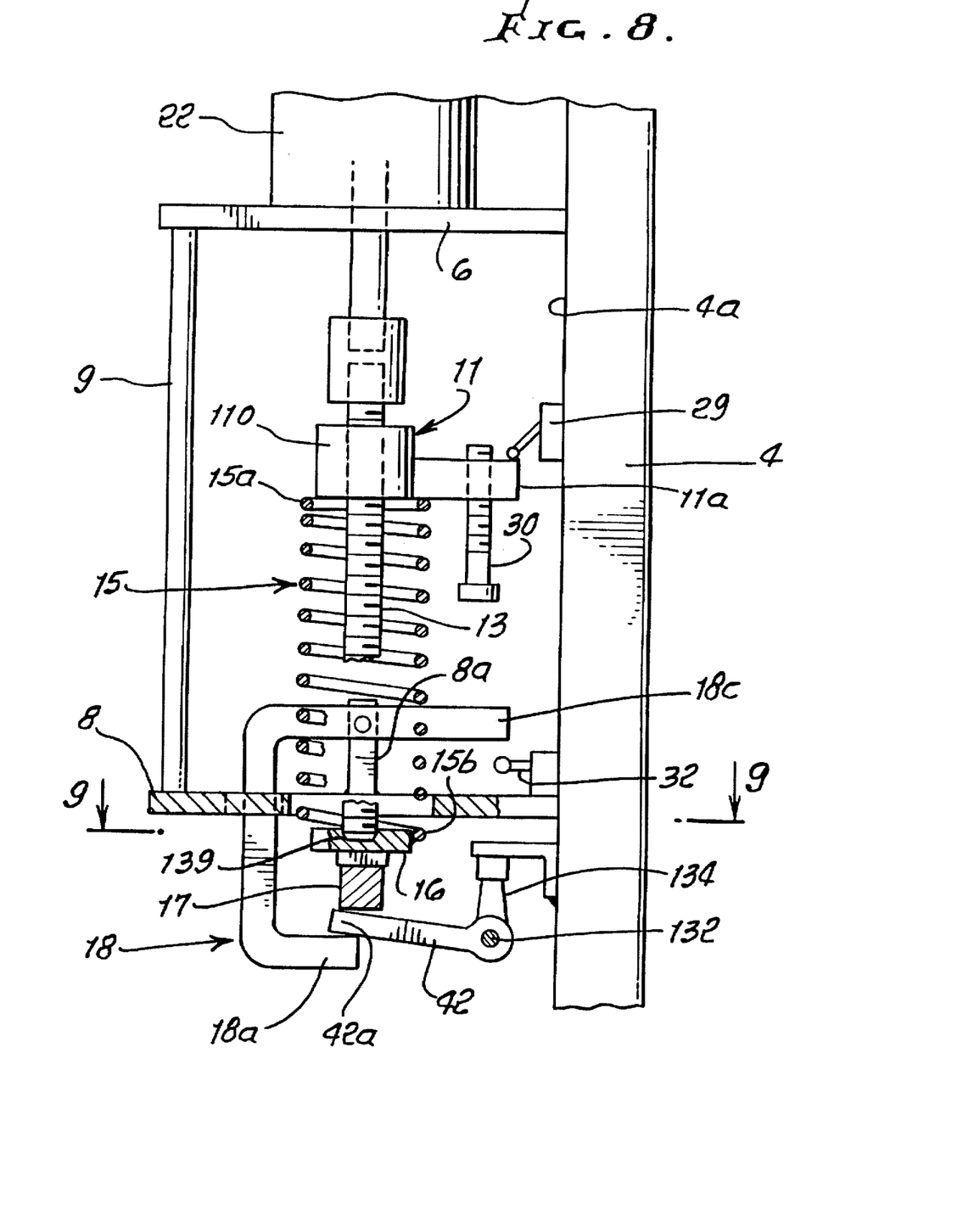
FIG. 8 is an enlarged partial cross-sectional side view of the latch mechanism portion of the accelerated impact testing apparatus, seen in FIG. 1.
Figure 9:
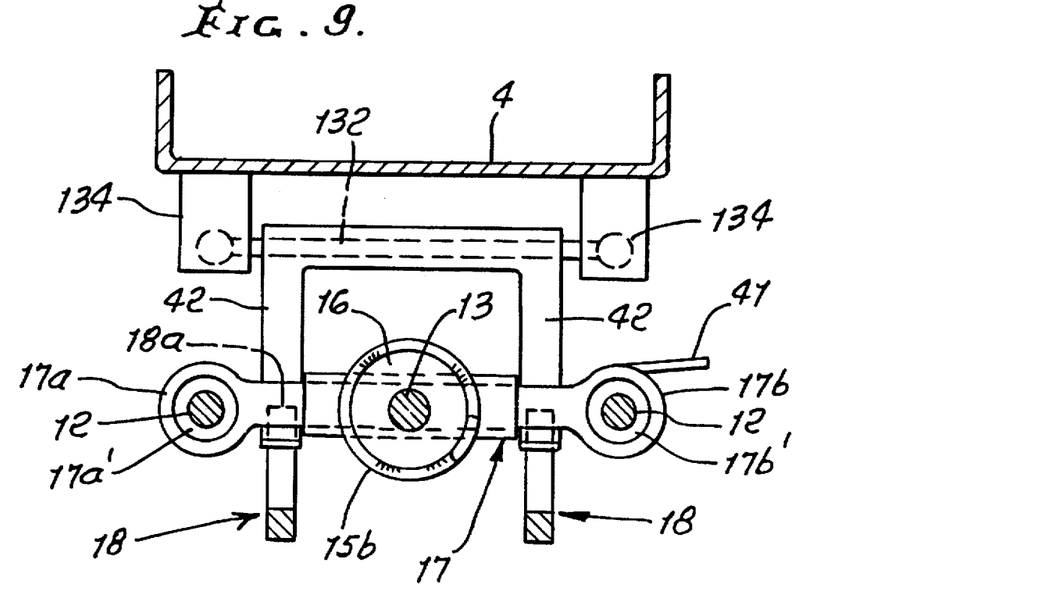
FIG. 9 is an enlarged cross-sectional plan view taken along lines 9—9 of FIG. 8, and illustrating the top of a pressure plate and cross head.

As best seen in FIG. 8 crosshead 17 is held in its uppermost position by restraining levers 42 and latch lever 18. The L-shaped levers 18 have pivot connection at 132 to posts 8a on plate 8, and levers 42 have pivot connection at 133 to brackets 134 attached to frame member 4. The hook ends 18a of levers 18 project beneath the ends 42a of levers 42, as seen in FIG. 8. Ends 42a project directly beneath crosshead 17. Rotation of ball screw 13 driven by motor 5 is transformed into a linear motion by ball nut 110 which is secured to spring compression assembly 11. Spring compression assembly 11 is restrained from rotating by the linear bearings at 17a' and 17b' riding on guide rails 12, as seen in FIG. 9. The lower end of screw 13 is centered in a coneshaped recess 139 in plate 16. See FIG. 8. The bottom end of spring 15 is attached to pressure plate 16 which distributes force to crosshead 17 (also see FIG. 9). The crosshead may consist of lightweight metal such as aluminum to reduce its acceleration mass.

Figure 12:
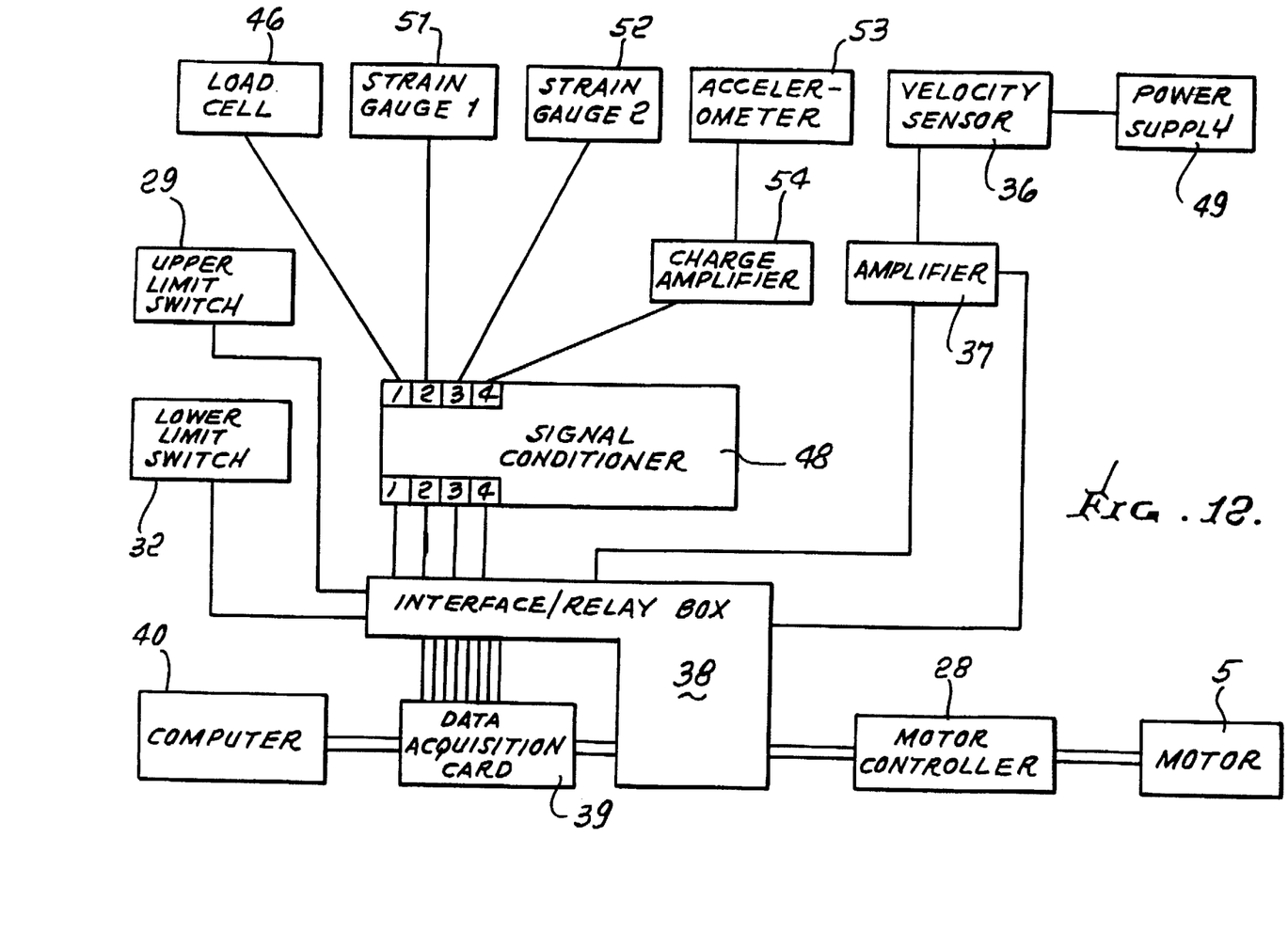
FIG. 12 is a block diagram showing electrical system circuitry usable to control the acceleration impact testing apparatus of FIGS. 1–11.

Referring to FIG. 12 operation of the accelerated impact test apparatus is controlled by computer 40 which executes a unique program developed for example with LabVIEW software. Other software can be used. The complete interface between computer 40 and the impact testing apparatus is make up of data acquisition card 39, interface/relay box 38 and signal conditioner 48. The test sequence begins by activating motor 5 which turns ball screw 13 and drives spring compression assembly 11 downward thus compressing spring 15 and applying force to pressure plate 16 and the restrained crosshead 17. The energy stored in spring 15 is predetermined and established by the length of an adjustable latch tripping bolt 30 threadably connected to part ill as shown. When latch tripping bolt 30 moves sufficiently downward, it engages and causes latch lever 18 upper lateral extent 18c to rotate about its pivot axis 132 (see FIG. 10), thereby removing under support from restraining lever 42 which immediately rotates about its pivot axis at 133 to avoid frictional forces, and allowing crosshead 17 to suddenly accelerate downward under force applied by spring 15. The continued downward motion of projecting extent 18c of latch lever 18 causes it to strike lower limit switch 32, which in turn interrupts electrical power to motor 5.

Figure 4:
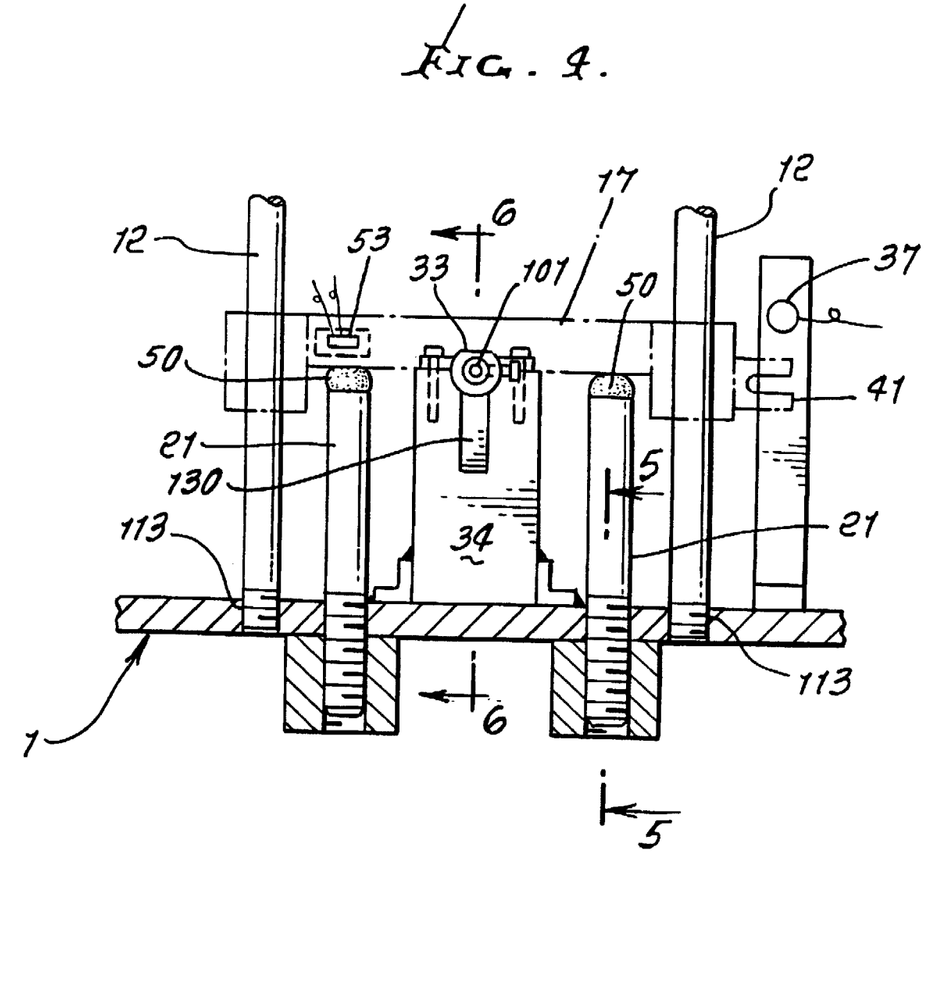
FIG. 4 is a partial cross-sectional elevational view taken along lines 4—4 of FIG. 3.
Figure 5:
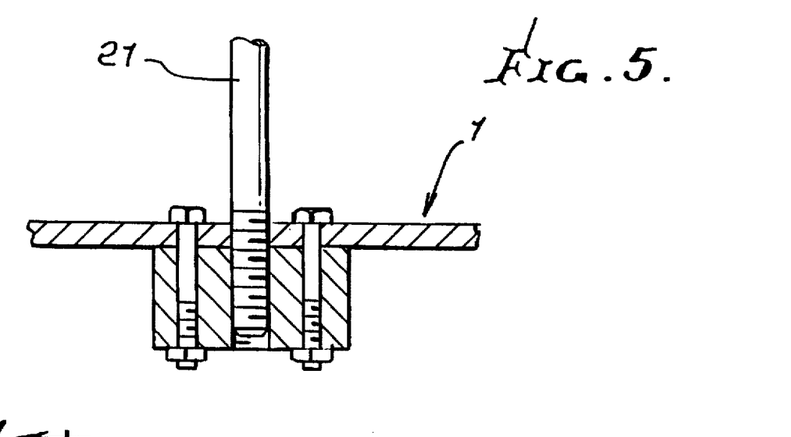
FIG. 5 is a partial cross-sectional elevational view of a bumper stop assembly taken along lines 5—5 of FIG. 4.
Figure 6:
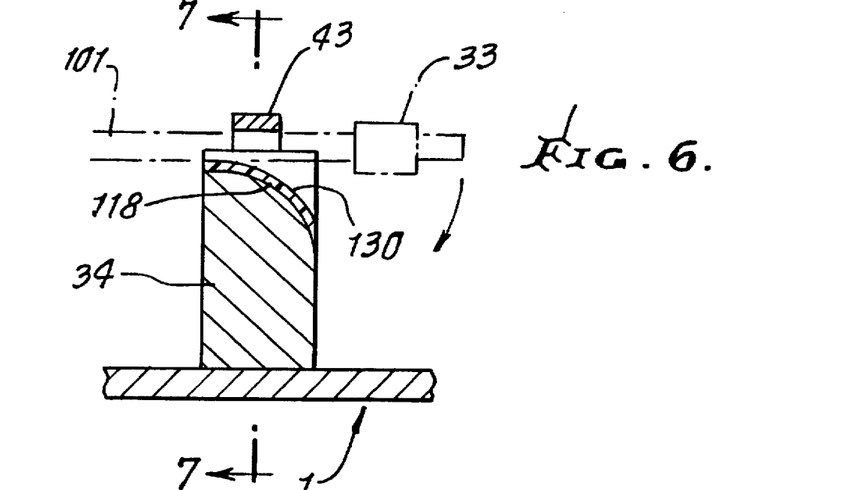
FIG. 6 is a partial cross-sectional elevational view of a front clamp taken along lines 6—6 of FIG. 4.
Figure 7:
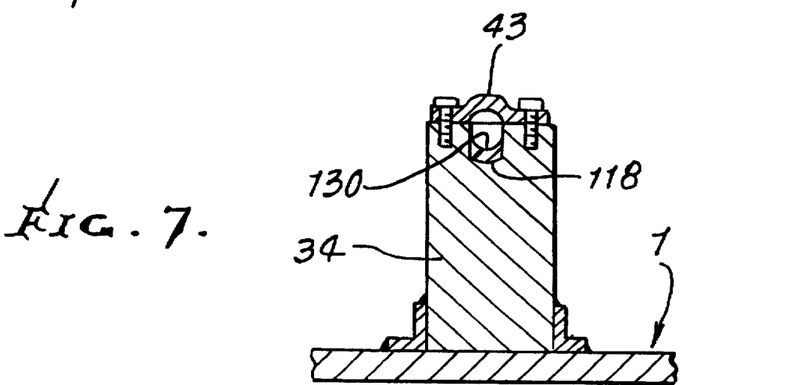
FIG. 7 is a cross-sectional elevational view of the front clamp taken along lines 7—7 of FIG. 6.

As best seen in FIG. 10 and FIG. 4, downward impelled traveling crosshead 17 with attached tup 19 strikes anvil sleeve 33 and imparts its kinetic energy to test specimen 101. The lowermost position of tup 19 is controlled by adjustable bumper stops 21 (see FIGS. 4 and 5) and bumper pads 50 which limit the downward travel of crosshead 17. The urethane pads 50 protect the crosshead from damage upon striking. The downward acceleration of crosshead 17 is measured by the output of accelerometer 53 carried by the crosshead 17, such output being amplified by charge amplifier 54 and transmitted to signal conditioner 48 for routing through interface/relay box 38 and data acquisition card 39 for recording by computer 40. The force applied by tup 19 is measured by the output of load cell 46 which is sent to signal conditioner 48 and routed through interface/relay box 38 and data acquisition card 39 for recording by computer 40. Spring 47 mounted in tup assembly 45 provides a constant calibration load for load cell 46 (see FIG. 11). Strain in test specimen 101 is measured by the outputs of strain gauge(#1) at 51 and strain gauge(#2) at 52 (see FIG. 10) which are sent to signal conditioner 48 and routed through interface/relay box 38 and data acquisition card 39 for recording by computer 40. Gauges 51 and 52 are attached to upper and lower sides of the shaft 101, as shown, between shaft first and second supports at 43 and 44, respectively.

Just prior to tup 19 striking tip sleeve or anvil 33, sensor flag 41 (see FIG. 4), attached to crosshead 17, interrupts the laser beam of velocity sensor 37. The laser emitter/receiver device is located about 0.25 inches from the flag. The velocity sensor signal is amplified by amplifier 36 and sent to interface/relay box 38 and in turn to data acquisition card 39. This information is used by computer 40 to determine the velocity and kinetic energy of tup 19 just prior to impact with test specimen 101. The output of sensor 37 is also transmitted to interface/relay box 38 to reverse the polarity of the signal controlling motor 5 and to apply electrical power to motor 5 to reverse rotate screw 23 and return spring compression assembly 11 to its uppermost position. Velocity sensor 37 is supplied with direct current by power supply 49.

It is to be understood that the above detailed description of a preferred embodiment of the invention is provided by way of example only. Many details of design and construction may be modified without departing from the true spirit and scope of the invention, as set forth in the appended claims.

I claim:

1. In testing apparatus for a golf shaft having a first end to support a grip, and a second end to support a club head, the combination comprising:
   a) primary means to support the shaft intermediate said first and second ends,
   b) secondary means to support the shaft near the second end and defining a lengthwise downwardly curved support channel into which the second end of the shaft is downwardly displaceable in response to impact loading, and
   c) a hammer located to be driven toward the shaft near the second end to deliver said impact loading to the shaft.

2. In testing apparatus for a golf shaft having a first end to support a grip, and a second end to support a club head, the combination comprising:
   a) primary means to support the shaft intermediate said first and second ends,
   b) secondary means to support the shaft near the second end and defining a lengthwise downwardly curved support channel into which the second end of the shaft is downwardly displaceable in response to impact loading,
   c) a hammer located to be driven toward the shaft near the second end to deliver said impact loading to the shaft,
   d) and including an anvil for placement on the shaft near the second end to be struck by the hammer.

3. In testing apparatus for a golf shaft having a first end to support a grip, and a second end to support a club head, the combination comprising:
   a) primary means to support the shaft intermediate said first and second ends,
   b) secondary means to support the shaft near the second end and defining a lengthwise downwardly curved support channel into which the second end of the shaft is downwardly displaceable in response to impact loading,
   c) a hammer located to be driven toward the shaft near the second end to deliver said impact loading to the shaft,
   d) and including a spring to be compressed and to suddenly expand toward the hammer, and a latch to retain the hammer until expanding spring force is delivered to the hammer, and to release the hammer in response thereto.

4. The apparatus of claim 3 including sensor means to sense the velocity of hammer travel as it delivers said impact loading.

5. The apparatus of claim 4 including circuitry responsive to said velocity sensing to compute the momentum of the hammer at impact.

6. The apparatus of claim 1 wherein said primary means includes a first support to support the shaft at a first location spaced from the shaft second end.

7. The apparatus of claim 1 including a clamp spaced from said primary means to clamp the shaft at a second location intermediate said primary means and the second end of the shaft.

8. In a method of testing a golf shaft having a first end to support a grip, and a second end to support a club head, the steps that include:

a) providing primary means supporting the shaft intermediate said first and second ends, b) providing secondary means supporting the shaft near the second end and defining a lengthwise downwardly curved support channel, c) and providing a hammer and driving the hammer toward the shaft near the second end to deliver impact loading to the shaft, thereby downwardly displacing the second end of the shaft into said channel.

9. In a method of testing a golf shaft having a first end to support a grip, and a second end to support a club head, the steps that include:

a) providing primary means supporting the shaft intermediate said first and second ends, b) providing secondary means supporting the shaft near the second end and defining a lengthwise downwardly curved support channel, c) and providing a hammer and driving the hammer toward the shaft near the second end to deliver impact loading to the shaft, thereby downwardly displacing the second end of the shaft into said channel, d) and including providing an anvil on the shaft near the second end and causing said anvil to be struck by the hammer.

10. In a method of testing a golf shaft having a first end to support a grip, and a second end to support a club head, the steps that include:

a) providing primary means supporting the shaft intermediate said first and second ends, b) providing secondary means supporting the shaft near the second end and defining a lengthwise downwardly curved support channel, c) and providing a hammer and driving the hammer toward the shaft near the second end to deliver impact loading to the shaft, thereby downwardly displacing the second end of the shaft into said channel, d) and including providing a spring to be compressed and to suddenly expand toward the hammer, and providing a latch to retain the hammer until expanding spring force is delivered to the hammer, and releasing the hammer in response thereto.

11. The method of claim 10 including providing and locating sensor means to sense the velocity of hammer travel as it delivers said impact loading.

12. The method of claim 11 including providing circuitry responsive to said velocity sensing to compute the momentum of the hammer at impact.

13. The method of claim 8, wherein said primary means is provided to include a first support supporting the shaft at a first location spaced from the shaft second end.

14. The method of claim 8 including providing a clamp spaced from said primary means to clamp the shaft at a second location intermediate said primary means and the second end of the shaft.

* * * * *